United States Patent [19]

Grasinger

[11] Patent Number: 5,230,699
[45] Date of Patent: Jul. 27, 1993

[54] PHALANX SPLINT

[76] Inventor: John E. Grasinger, 139 Hunting Cove, Williamsburg, Va. 23185

[21] Appl. No.: 835,861

[22] Filed: Feb. 18, 1992

[51] Int. Cl.$^5$ .............................................. A61F 5/04
[52] U.S. Cl. ...................................... 602/22; 128/880
[58] Field of Search .................. 602/5, 12, 15, 21, 22, 602/30, 23, 58; 128/880, DIG. 20

[56] References Cited

U.S. PATENT DOCUMENTS

| | | | |
|---|---|---|---|
| 1,404,906 | 1/1922 | Strahl | 602/22 |
| 4,294,237 | 10/1981 | Frazier | 602/21 |
| 4,441,489 | 4/1984 | Evans | 602/22 |
| 4,456,002 | 6/1984 | Barber | 602/22 |
| 4,662,364 | 5/1987 | Viegas | 602/21 |
| 4,829,988 | 5/1989 | Caminiti | 602/22 |
| 4,944,290 | 7/1990 | Hepburn | 602/22 |

Primary Examiner—Robert A. Hafer
Assistant Examiner—David J. Kenealy
Attorney, Agent, or Firm—Peter J. Van Bergen

[57] ABSTRACT

A finger splint is provided for immobilizing a fracture of a finger's middle or proximal phalanx. A hinged splint body cradles a finger with a fractured phalanx. A hinging portion of the splint body is positioned beneath an interphalangeal joint located immediately adjacent and distal to the fractured phalanx. A fulcrum is placed between the splint body and the finger and is positioned directly beneath the fractured phalanx's line of fracture. Means are provided for securing the splint body and fulcrum in place such that the splint body is free to move about the hinged portion thereof in correspondence with a portion of the finger located distally with respect to the fractured phalanx. In this way, the fulcrum exerts an upward reduction force on the fractured phalanx at the fracture line. Furthermore, the finger splint simultaneously allows motion by adjacent joints both distal and proximal to the fracture to encourage a dynamic reduction of the fracture.

13 Claims, 2 Drawing Sheets

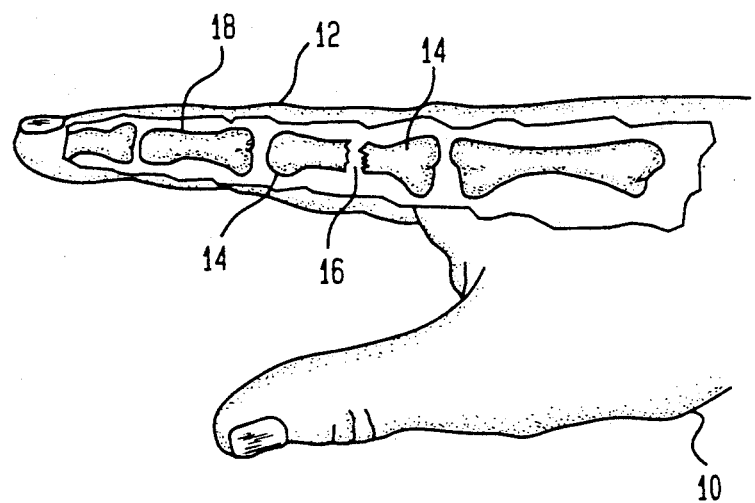
FIG. 1
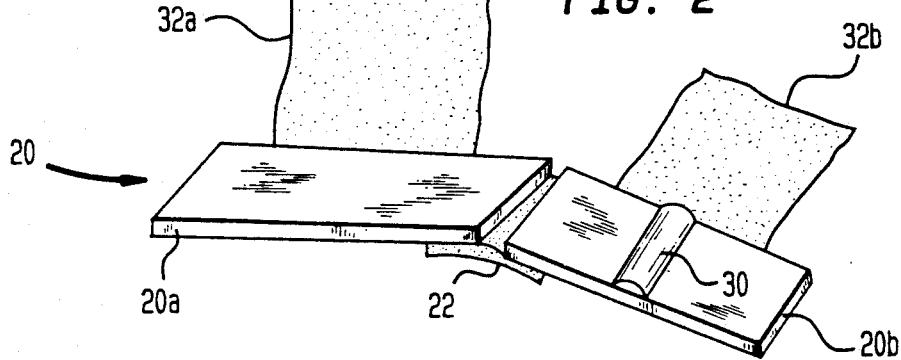
FIG. 2
FIG. 3
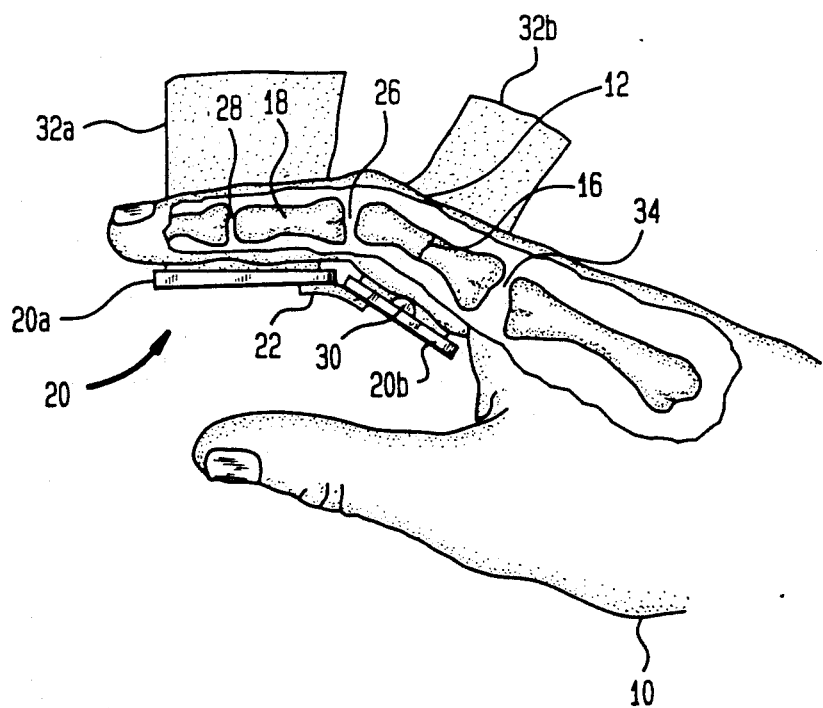

PHALANX SPLINT

FIELD OF THE INVENTION

The invention relates generally to splints, and more particularly to a finger splint for use in the reparation of a finger's fractured middle or proximal phalanx.

BACKGROUND OF THE INVENTION

Fractures of a finger's middle or proximal phalanx have traditionally been immobilized in a reduced position in one of two ways. One approach is surgical in nature and involves the insertion of pins or screws to stabilize or reduce the fracture. A second, non-surgical approach, involves casting the hand, wrist and distal forearm in cooperation with an outrigger splint to hold the fractured finger. However, each of these approaches is inherently flawed in that each fosters various medical side effects that may necessitate further medical treatment.

For example, the surgical approach traumatizes the surrounding tissue, muscles and bone structure thereby increasing the amount of post operative therapy required for proper healing. In addition, surgery always introduces the possibility of infection. The non-surgical splint approach requires that the finger be splinted in a crooked position in order to prevent the finger's extensor tendons from causing the fracture to angulate. This approach has two major drawbacks. First, immobilization of the fracture in a properly reduced position also inconveniently immobilizes the patient's hand. Secondly, immobilizing the finger in the crooked position pulls the extensor tendon onto the healing fracture. This may cause the callus formed during healing to adhere to the extensor tendon. Therefore, once the splint is removed, it is sometimes necessary to surgically release the tendon from the newly formed bone. Furthermore, even if such surgery is not required, joints adjacent to the fracture stiffen while the finger is splinted. Accordingly, some therapy is required to restore the finger's flexing mobility once the cast and splint are removed.

SUMMARY OF THE INVENTION

Accordingly, it is an object of the present invention to provide a non-surgical approach to properly reduce a fracture of the middle or proximal phalanx that is free from medical side effects and thereby reduces the overall healing time for such an injury.

Another object of the present invention is to provide a finger splint that properly reduces a fracture of the middle or proximal phalanx, and, at the same time allows joints adjacent to the fractured phalanx to be mobile thereby affording the patient some degree of dexterity during the healing process.

Still another object of the present invention is to provide a finger splint that dynamically reduces a fracture of the middle or proximal phalanx by allowing mobility in the joints adjacent to the fractured phalanx.

Yet another object of the present invention is to provide a finger splint that is small, lightweight and inexpensive to manufacture.

Other objects and advantages of the present invention will become more obvious hereinafter in the specification and drawings.

In accordance with the present invention, a finger splint is provided for immobilizing a fracture of a finger's middle or proximal phalanx. The finger splint simultaneously allows motion by adjacent joints both distal and proximal to the fracture to encourage a dynamic reduction of the fracture. A hinged splint body cradles a finger with a fractured phalanx. A hinging portion of the splint body is positioned beneath an interphalangeal joint located immediately adjacent and distal to the fractured phalanx. A fulcrum is placed between the splint body and the finger. The fulcrum is further positioned directly beneath the fractured phalanx's line of fracture in a direction substantially transverse with respect to a longitudinal axis of the fractured phalanx in a reduced position. Means are provided for securing the splint body and fulcrum in place such that the splint body is free to move about the hinged portion thereof in correspondence with a portion of the finger located distally with respect to the fractured phalanx. In this way, the fulcrum exerts an upward reduction force on the fractured phalanx at the fracture line.

BRIEF DESCRIPTION OF THE DRAWINGS

FIG. 1 is a side view of a hand showing the bone structure of its index finger in isolation;

FIG. 2 is a perspective view of a preferred embodiment of the phalanx splint according to the present invention;

FIG. 3 is a side view of the hand and finger of FIG. 1 fitted with the phalanx splint of the present invention;

DETAILED DESCRIPTION OF THE INVENTION

Figure 4:
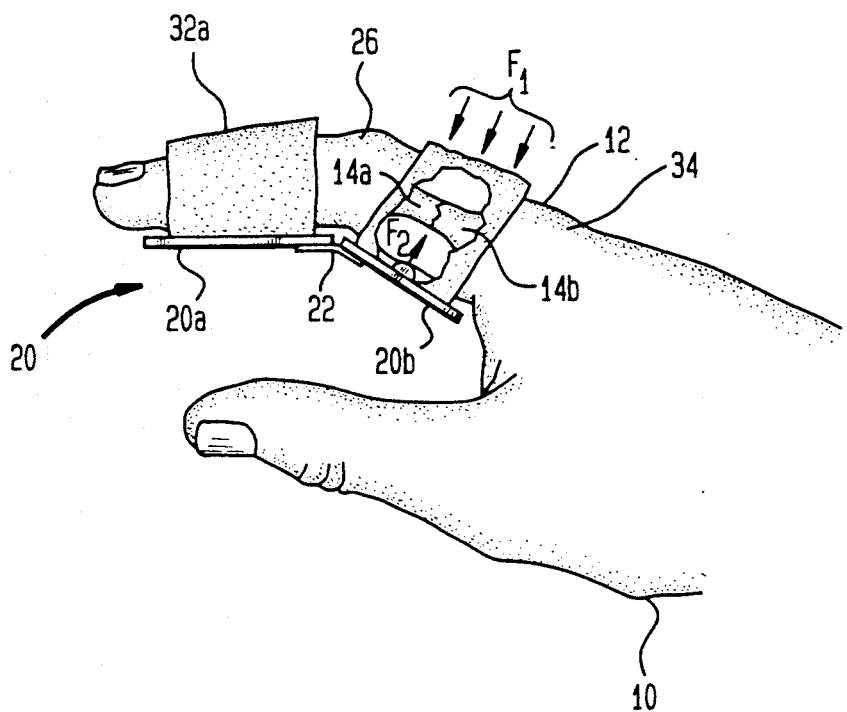
FIG. 4 is a side view of the hand and finger of FIG. 3 fitted with the phalanx splint showing the particular forces applied by the phalanx splint.

Referring now to the drawings, and more particularly to FIG. 1, a side view of a hand 10 is shown with a partial cutaway view of the index finger 12 to expose the bone structure thereof in isolation. Specifically, the proximal phalanx 14 is shown to have a fracture 16 (exaggerated for purposes of illustration). While the present invention will be described in detail with respect to this fracture, it will be readily understood that the teachings of the present invention apply equally as well to a fracture of the middle phalanx 18.

The present invention will now be described with simultaneous reference to FIGS. 2-4. In FIG. 2, a perspective view of splint 20 is shown in isolation. FIG. 3 is a side view of hand 10 having a preferred embodiment of splint 20 positioned underneath index finger 12 and FIG. 4 is a side view of the hand and finger of FIG. 3 fitted with the phalanx splint showing the particular forces applied by the phalanx splint. Like reference numerals are used for like elements in FIGS. 2-4. Splint 20 is formed from two rigid plate-like sections 20a and 20b that are joined together in flexible relationship by flexing hinge 22. Sections 20a and 20b may be made from any common, nonflexing splint material such as plastic or aluminum. Hinge 22 may be a flexible material (i.e. cloth, rubber, etc.) serving as a bridge that is adhered to and connects sections 20a and 20b. Alternatively, hinge 22 may be a conventional fixed hinge (see FIG. 5).

Hinge 22 is positioned under the proximal interphalangeal joint 26 such that as joint 26 flexes, splint section 20a moves in correspondence therewith as allowed by hinge 22. (For a fracture of the middle phalanx 18, splint section 20b would be positioned under same while hinge 22 would be positioned underneath the distal interphalangeal joint 28.)

Provided between splint section 20b and index finger 12 is a fulcrum 30 placed directly beneath fracture 16 as it is held in its reduced position to form a line of fracture. Placement of fulcrum 30 may be achieved in a variety of ways. Fulcrum 30 could be glued in place on splint section 20b with an adhesive or removably secured in place by a hook and loop fastening system. Alternatively, fulcrum 30 could be integral with splint section 20b. In such an alternative, splint section 20b could be trimmed to size depending on the size of the patient's finger and location of the fracture.

For reasons that will become more clear hereinbelow, fulcrum 30 would ideally be shaped to have a single line of contact with finger 12. The single line of contact should be in a direction that is substantially transverse to the longitudinal axis of proximal phalanx 14 in its reduced position. However, for patient comfort, fulcrum 30 is typically semi-circular in cross-section and is positioned such that the middle of its arcuate surface s directly beneath fracture 16 as shown in FIG. 3. Fulcrum 30 is typically made from a resilient yet firm material in order to protect the skin on finger 12. Typically, fulcrum 30 may be made of rubber (natural or synthetic), a synthetic polymer exhibiting the properties of rubber, or a felt/cloth roll.

To secure splint 20 in the aforedescribed position, two (or more) tension straps 32a and 32b are wrapped about finger 12 as shown in FIG. 4. Specifically, strap 32a secures splint section 20a to the portion of finger 12 located distally to the proximal interphalangeal joint 26. Strap 32b secures splint section 20b and fulcrum 30 (shown in the cutaway portion of strap 32b) to the portion of finger 12 associated with the (fractured) proximal phalanx 14 in order to immobilize same in the reduced position. In this way, the patient is able to flex index finger 12 at both the proximal interphalangeal joint 26 and the metacarpal phalangeal joint 34.

Straps 32a and 32b may be integral with (as shown) or separate from their respective splint sections 20a and 20b. Straps 32a and 32b may have hook and loop fastener capability. Alternatively, straps 32a and 32b might be equipped with a self adhesive strip (not shown). Other suitable tension adjusting mechanisms may be used as desired.

As shown in FIG. 4, strap 32b is tensioned to deliver an evenly distributed force designated by force arrows $F_1$. Simultaneously, the tension in strap 32b causes a concentrated upward force $F_2$ directed through fulcrum 30 at the fracture 16. This counter or fulcrum force helps to maintain the fracture 16 in its reduced position. The balancing of forces further ensures that the distal portion 14a of proximal phalanx 14 does not angulate with respect to the proximal portion 14b. Thus, surgically inserted pins are screws are no longer needed to prevent angulation.

Furthermore, by allowing the finger to flex at the joints immediately proximal and distal to the fractured phalanx, a dynamic reduction of the fracture is achieved. For the case described, finger 12 may flex at its metacarpal phalangeal joint 34 and its proximal interphalangeal joint 26. (In the case of a middle phalanx fracture, splint 20 would be configured to permit flexing at the distal interphalangeal joint 28 and the proximal interphalangeal joint 26.) Such a dynamic reduction eliminates the adherence of the extensor tendons to callus forming around fracture 16. Thus, no surgery would ever be required to releases tendon adhesion after splint 20 is removed. Finally, by allowing the joints adjacent to the fractured phalanx to flex, joint stiffness is minimized once splint 20 is removed.

Figure 5:
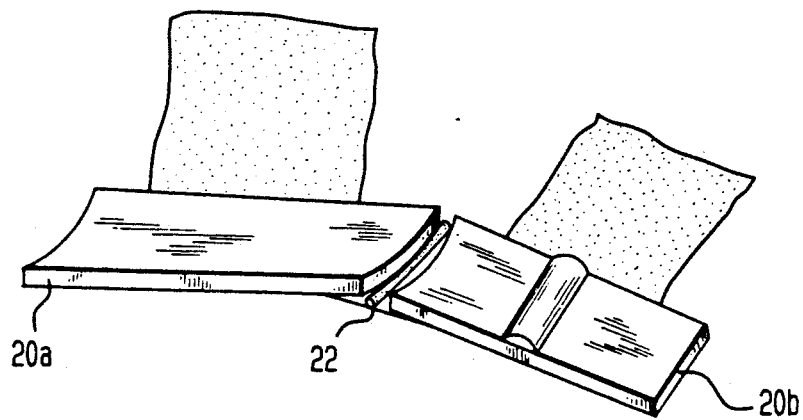
FIG. 5 is a perspective view of an alternative embodiment of the phalanx splint.

Although the invention has been described relative to a specific embodiment thereof, there are numerous variations an modifications that will be readily apparent to those skilled in the art in the light of the above teachings. For example, splint sections 20a and 20b could be slightly shaped to cradle a finger as shown in FIG. 5. Also, an air breathing pad (not shown) such as felt or gauze might be placed on each splint section 20a and 20b that comes into contact with the finger being splinted. Finally, hinge 22 might alternatively be a conventional fixed hinge that allows movement between sections 20a and 20b as described above. It is therefore to be understood that, within the scope of the appended claims, the invention may be practiced other than as specifically described.

What is claimed and desired to be secured by Letters Patent of the United States is:

1. A finger splint for immobilizing a fracture of a finger's middle or proximal phalanx and for simultaneously allowing unimpeded motion by adjacent joints both distal and proximal to the fracture to encourage a dynamic reduction of the fracture, comprising:
    a first splint portion adapted to be secured about a finger's fractured phalanx, said first splint portion including a raised portion being arcuately shaped to tangentially contact the finger under the line of fracture, said raised portion further having a longitudinal axis that is substantially transverse to a longitudinal axis of the fractured phalanx to deliver an upward force concentrated at the fracture line, said first splint body portion further including means for delivering a downward force evenly distributed on both sides of the fracture line all along the fractured phalanx;
    a second splint portion adapted to be secured to a portion of the finger that is distal with respect to the fractured phalanx; and
    a material, pivotally connecting said first and second splint portions under an interphalangeal joint adjacently distal to the fractured phalanx, for permitting unimpeded movement of said second splint portion as controlled by movement of the portion of the finger that is distal with respect to the fractured phalanx, the unimpeded movement occurring within the fractured finger's natural radial plane of motion wherein said second splint portion is free to move in correspondence with actively induced and passively induced motion of the portion of the finger that is distal with respect to the fractured phalanx.

2. A finger splint as in claim 1 wherein said fist and second splint portions comprise a rigid material.

3. A finger splint as in claim 2 wherein the rigid material is plastic.

4. A finger splint as in claim 2 wherein the rigid material is aluminum.

5. A finger splint as in claim 1 wherein said first and second splint portions are slightly concave in shape to cradle the finger.

6. A finger splint as in claim 1 wherein said said raised portion comprises a resilient material.

7. A finger splint as in claim 6 wherein said resilient material is selected from the group consisting of synthetic rubber, natural rubber and synthetic polymers.

8. A finger splint as in claim 6 wherein said resilient material comprises felt.

9. A finger splint as in claim 1 wherein said means for delivering a downward force comprises an adjustable tension strap for securing said first splint portion to the finger.

10. A finger splint as in claim 9 wherein said adjustable tension strap includes hook and loop fastener portions thereon.

11. A finger splint as in claim 9 wherein said adjustable tension strap includes an integral adhesive.

12. A finger splint s in claim 1 wherein said raised portion is integral with said first splint portion.

13. A finger splint as in claim 1 wherein said raised portion is attachable to said first splint portion.

* * * * *